United States Patent
Attawia et al.

(10) Patent No.: US 9,474,912 B2
(45) Date of Patent: *Oct. 25, 2016

(54) RED LIGHT IMPLANTS FOR TREATING OSTEOPOROSIS

(71) Applicant: DePuy Synthes Products, LLC, Raynham, MA (US)

(72) Inventors: Mohamed Attawia, Holmdel, NJ (US); Thomas M DiMauro, Southboro, MA (US); Jeffrey K Sutton, Wilton Manors, FL (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 71 days.

This patent is subject to a terminal disclaimer.

(21) Appl. No.: 14/499,520

(22) Filed: Sep. 29, 2014

(65) Prior Publication Data
US 2015/0073558 A1 Mar. 12, 2015

Related U.S. Application Data

(63) Continuation of application No. 13/587,542, filed on Aug. 16, 2012, now Pat. No. 8,845,703, which is a continuation of application No. 11/235,674, filed on Sep. 26, 2005, now Pat. No. 8,262,713.

(51) Int. Cl.
*A61F 2/44* (2006.01)
*A61B 17/86* (2006.01)
*A61N 5/06* (2006.01)

(52) U.S. Cl.
CPC ............ *A61N 5/0613* (2013.01); *A61B 17/86* (2013.01); *A61F 2/44* (2013.01); *A61N 5/0601* (2013.01); *A61N 2005/0643* (2013.01); *A61N 2005/0651* (2013.01); *A61N 2005/0659* (2013.01); *A61N 2005/0663* (2013.01)

(58) Field of Classification Search
CPC ...... A61B 17/86; A61F 2/44; A61N 5/0601; A61N 5/0613; A61N 2005/0651; A61N 2005/0659; A61N 2005/0643; A61N 2005/0663
USPC ........... 623/17.16, 23.72; 606/328, 821, 279, 606/11, 9, 300–321; 607/51, 88–94; 128/898; 600/476, 473; 424/423
See application file for complete search history.

(56) References Cited

U.S. PATENT DOCUMENTS

| | | | |
|---|---|---|---|
| 5,201,729 A | 4/1993 | Hertzmann |
| 5,259,380 A | 11/1993 | Mendes |
| 5,401,270 A | 3/1995 | Muller |
| 5,445,608 A | 8/1995 | Chen |
| 5,607,426 A | 3/1997 | Ralph |

(Continued)

FOREIGN PATENT DOCUMENTS

| | | |
|---|---|---|
| EP | 1348390 | 10/2003 |
| EP | 1021223 | 10/2004 |

OTHER PUBLICATIONS

Akai, "Laser's effect on bone and cartilage chance induced by joint immobilization: an experiment with animal model", *Laser Surg Med.*, 1997, pp. 480-484, vol.21(5).

(Continued)

*Primary Examiner* — Pedro Philogene
(74) *Attorney, Agent, or Firm* — Thomas M. DiMauro

(57) ABSTRACT

Red light implants for delivering red light to spinal implants to enhance osteointegration.

7 Claims, 8 Drawing Sheets

(56) References Cited

U.S. PATENT DOCUMENTS

| | | | |
|---|---|---|---|
| 5,609,636 A | 3/1997 | Kohrs | |
| 5,616,140 A | 4/1997 | Prescott | |
| 5,640,978 A | 6/1997 | Wong | |
| 5,643,265 A | 7/1997 | Errico | |
| 5,800,478 A | 9/1998 | Chen | |
| 5,843,082 A | 12/1998 | Yuan | |
| 5,876,402 A | 3/1999 | Errico | |
| 5,904,683 A | 5/1999 | Pohndorf | |
| 5,948,008 A | 9/1999 | Daikuzono | |
| 5,989,245 A | 11/1999 | Prescott | |
| 6,017,345 A | 1/2000 | Richelsoph | |
| 6,036,345 A | 3/2000 | Jannette | |
| 6,063,108 A | 5/2000 | Salansky | |
| 6,073,051 A | 6/2000 | Sharkey | |
| 6,179,875 B1 | 1/2001 | Von Strempel | |
| 6,206,882 B1 | 3/2001 | Cohen | |
| 6,214,012 B1* | 4/2001 | Karpman | A61B 17/864 606/246 |
| 6,241,731 B1 | 6/2001 | Fiz | |
| 6,270,492 B1* | 8/2001 | Sinofsky | A61L 2/10 606/13 |
| 6,322,562 B1 | 11/2001 | Wolter | |
| 6,402,756 B1 | 6/2002 | Ralph | |
| 6,409,719 B1 | 6/2002 | Manning | |
| 6,428,542 B1 | 8/2002 | Michelson | |
| 6,454,769 B2 | 9/2002 | Wagner | |
| 6,494,900 B1 | 12/2002 | Salansky | |
| 6,503,269 B2 | 1/2003 | Nield | |
| 6,537,304 B1 | 3/2003 | Oron | |
| 6,575,975 B2 | 6/2003 | Brace | |
| 6,599,290 B2 | 7/2003 | Bailey | |
| 6,733,496 B2 | 5/2004 | Ashley | |
| 6,749,605 B2 | 6/2004 | Ashley | |
| 6,866,678 B2* | 3/2005 | Shenderova | A61N 5/0616 128/898 |
| 6,890,334 B2 | 5/2005 | Brace | |
| 6,974,480 B2 | 12/2005 | Messerli | |
| 7,001,389 B1 | 2/2006 | Navarro | |
| 7,056,341 B2 | 6/2006 | Crozet | |
| 7,131,963 B1* | 11/2006 | Hyde | A61B 17/22 604/101.01 |
| 7,455,672 B2 | 11/2008 | Michelson | |
| 7,465,313 B2 | 12/2008 | DiMauro | |
| 8,262,713 B2* | 9/2012 | Attawia | A61B 17/86 128/898 |
| 8,845,703 B2* | 9/2014 | Attawia | A61B 17/86 128/898 |
| 2002/0045922 A1 | 4/2002 | Nield | |
| 2002/0058939 A1 | 5/2002 | Wagner | |
| 2002/0087206 A1 | 7/2002 | Hirschberg | |
| 2002/0138073 A1 | 9/2002 | Intintoli | |
| 2002/0138146 A1 | 9/2002 | Jackson | |
| 2003/0004576 A1 | 1/2003 | Thalgott | |
| 2003/0125782 A1 | 7/2003 | Streeter | |
| 2003/0225331 A1 | 12/2003 | Diederich | |
| 2004/0106996 A1 | 6/2004 | Liu et al. | |
| 2004/0111132 A1 | 6/2004 | Shenderova | |
| 2004/0127899 A1 | 7/2004 | Konieczynski | |
| 2005/0085910 A1* | 4/2005 | Sweeney | A61F 2/44 623/17.11 |
| 2005/0228386 A1 | 10/2005 | Ziolo | |
| 2006/0206172 A1 | 9/2006 | DiMauro | |
| 2006/0229729 A1 | 10/2006 | Gordon et al. | |
| 2006/0271131 A1 | 11/2006 | Passy | |
| 2006/0287695 A1 | 12/2006 | DiMauro | |
| 2007/0073300 A1 | 3/2007 | Attawia | |
| 2008/0154377 A1 | 6/2008 | Voellmicke | |

OTHER PUBLICATIONS

Ariga, "Mechanical stress-induced apoptosis of endplate chondrocytes in organ-cultured mouse intervertebral discs", *Spine*, 2003, pp. 1528-1533, vol. 28(14), Lippincott Willian & Wilkins, Inc.

Bai, "Augmentation of Anterior Vertebral Body Screw Fixation by an Injectable", Biodegradable Calcium Phosphate Bone Substitute, *Spine*, 2001, pp. 2679-2683, vol. 26(24).

Bayat, "Effect of low-power helium—neon laser irradiation on 13-week immobilized articular cartilage of rabbits", *Indian J Exp Biol.*, 2004, pp. 866-860, vol. 42(9).

Bjordal, "A systematic review of low level laser therapy with location-specific doses for pain from chronic joint disorders", *Australian Journal of Physiotherapy*, 2003, pp. 107-116, vol. 49.

Borenstein, "Epidemiology, etiology, diagnostic evaluation and treatment of low back pain", *Curr Opin Rheumatol*, 1999, pp. 15-17, vol. 11(2).

Bossy, "In vitro survey of low energy laser beam penetration in compact bone", *Acupunct Electrother Res.*, 1985, pp. 35-39, vol. 10(1-2).

Carnevalli, "Laser light prevents apoptosis in Cho K-1 cell line", *J Clin. Laser Med Surg*, 2003, pp. 193-196, vol. 21(4), Mary Ann Liebert, Inc.

Cho, "Effect of low-level laser therapy on Osteoarthropathy in Rabbit", *In Vivo*, 2004, pp. 585-592, vol. 18.

Cook, "Biomechanical study of pedicle screw fixation in severely osteoporotic bone", *Spine Journal*, 4 (2004) 402-8.

Cook, "Lumbosacral fixation using expandable pedicle screws: an alternative in reoperation and osteoporosis", *Spine Journal*, 1(2001) 109-114.

Del Carlo, "Nitric oxide-mediated chondrocyte cell death requires the generation of additional reactive oxygen species", Arthritis Rheum., 2002, pp. 394-403, vol. 46(2).

Dortbudak, "Effect of low-power laser irradiation on bony implant sites"; Clin. Oral Implants Res., 2002, Jun. 13(3) 288-92.

Ebert, "Effect of irradiation with a low-intensity diode laser on the metabolism of equine articular cartilage in vitro", *Am J Vet Res.*, 1998, pp. 1613-1618, vol. 59(12).

Guzzardella, "Assessment of low-power laser biostimulation on chondral lesions: an "in vivo" experimental study", *Artif Cells Blood Substit Immobil Biotechnol.*, 2000, pp. 441-449, vol. 28(5).

Guzzardella, "Cartilage cell stimulation with low-power laser: experimental assessment", Acta Bio-Medica, 1999, pp. 43-47, vol. 70(3-4) [See English Abstract as provided].

Guzzardella, "Laser stimulation on bone defect healing: an in vitro study", *Lasers Med Sci.*, 2002, pp. 216-220, vol. 17(3).

Guzzardella, "Laser Technology in Orthopedics: Preliminary Study on Low Power Laser Therapy to Improve the Bone-Biomaterial Interface"; *Int. J. Artif. Organs*, Dec. 2001 24(12): 898-902.

Guzzardella, "Low-power diode laser stimulation of surgical osteochondral defects: results after 24 weeks", *Artif Cells Blood Substit Immobil Biotechnol.*, 2001, pp. 235-244, vol. 29(3).

Hamajima, "Effect of low-level laser irradiation on osteoglycin gene expression in osteoblasts", *Laser Med Sci*, 2003 vol. 18 (2) pp. 78-82.

Herman, "In vitro effects of Nd:YAG laser radiation on cartilage metabolism", *J Rheumatol*, 1988, pp. 1818-1826, vol. 15(12).

Iwatsuki, "The effect of laser irradiation for nucleus pulposus: an experimental study", *Neurol Res*, 2005, pp. 319-323, vol. 27(3), W. S Maney & Son.

Jia, "Effect of low-power he—ne laser irradiation on rabbit articular chondrocytes in vitro", *Lasers in Surgery and Medicine*, 2004, pp. 323-328, vol. 34, Wiley-Liss, Inc.

Jouzeau, "Nitric oxide (NO) and cartilage metabolism: NO effects are modulated by superoxide in response to IL-1", Biorheology, 2002, pp. 201-214, vol. 39(1-2).

Khandra, "Effect of LLLT on Implant-tissue Interaction"; Swed. Dent. J. Suppl., 2005, (172) 1-63.

Khandra, "Laser Therapy Accelerates Initial Attachment and Subsequent Behaviour of Human Oral Fibriblasts Cultured on Titanium Implant Material"; Clin Oral Implants Res., Apr. 2005 16(2) 168-75.

Khandra, "Low-level Laser Therapy Stimulates bone-Implant Interaction: An Experimental Study in Rabbits"; *Clin. Oral Implants Res.*, Jun. 2004:15(3):325-332.

Khanna, "Augmentation of the expression of proangiogenic genes in cardiomyocytes with low dose laser irradiation in vitro", *Cardiovasc Radiat Med.*, 1999, pp. 265-269, vol. 1(3).

(56) References Cited

OTHER PUBLICATIONS

Kipshidze, "Low-power helium: neon laser irradiation enhances production of vascular endothelial growth factor and promotes growth of endothelial cells in vitro", *Lasers Surg Med*, 2001, pp. 355-364, vol. 28(4).

Kolari, "Poor penetration of infra-red and helium neon low poser laser light into the dermal tissue", *Acupunct Electrother Res.*, 1993, pp. 17-21, vol. 18(1).

Kolarova, "Penetration of the laser light into the skin in vitro", *Lasers Surg Med.*, 1999, pp. 231-235, vol. 24(3).

Lin, "Effects of helium-neon laser on levels of stress protein and arthritic hist", *Am J. Phys Med Rehabil*, 2004, pp. 758-765, vol. 83(10), Lippincott, Williams & Wilkins.

Lopes, "Infrared Laser Light Reductes Loading Time of Dental Implants: A Raman Spectroscopic Study"; *Photomed. Laser Surg,.* Feb. 2005, vol. 23(1,)pp. 27-31.

Matsushuta, "Hypoxia-induced nitric oxide protects chondrocytes from damage by hydrogen peroxide", *Inflamm Res.*, 2004, pp. 344-350, vol. 53(8). Epub Aug. 2004.

Morrone, "Biostimulation of human chondrocytes with Ga—Al—As diode laser:'in vitro'", *Artif Cells Blood Substit Immobil Biotechnol*, 2000, pp. 193-201, vol. 28(2).

Nerlich, "1997 Volvo Award winner in basic science studies. Immunohistologic markers for age-related changes of human lumbar intervertebral discs", *Spine*, 1997, pp. 2781-1795, vol. 22(24).

Notzli, "Laser Doppler flowmetry for bone blood flow measurements: helium—neon laser light attenuation and depth of perfusion assessment", *J Orthop Res.*, 1989, pp. 13-424, vol. 7(3).

Pullin, "Effects of holmium: YAG laser energy on cartilate metabolism, healing and biochemical properties of lesional and perilesional tissue in a weight-bearing model", *Arthroscopy*, 1996, pp. 15-25, vol. 12(1).

Rannou,"Intervertebral Disc Degeneration", *American Journal of Pathology*, 2004, pp. 915-924, vol. 164(3), American Society for Investigative Pathology.

Reed, "An in vivo study of the effect of excimer laser irradiation on degenerate rabbit articular cartilage", *Arthroscopy*, 1994, pp. 78-84, vol. 10(1).

Schemitsch, "Evaluation of a laser Doppler flowmetry implantable fiber system for determination of threshold thickness for flow detection in bone", *Calcif Tissue Int.*, 1994, pp. 216-222, vol. 55(3).

Schultz, "Effects of varying intensities of laser energy on articular cartilage: a preliminary Study", *Laser Surg Med*, 1958, pp. 577-588, vol. 5(6).

Shefer, "Low-energy laser irradiation promotes the survival and cell cycle entry of skeletal muscle satellite cells", *Journal of Cell Science*, 2002, pp. 1461-1469, vol. 115, The company of Biologists Ltd.

Spivak, "The effect of low-level Nd:YAG laser energy on adult articular cartilage in vitro", *Arthroscopy: The Journal of Arthroscopc and Related Surgery*, 1992, pp. 36-43, vol. 8(1), Raven Press Ltd.

Torricelli, "Laser biostimulation of cartilage: in vitro evaluation", Biomed Pharmacother, 2001, pp. 117-120, vol. 55.

Wang, "Measuring dynamics of caspase-3 activity in living cells using FRET technique during apoptosis induced by high fluence low-power laser irradiation", Lasers Surg Med., 2005, pp. 2-7, vol. 36(1).

Wong-Riley, "Photobiomodulation directly benefits primary neurons functionally inactivated by toxins", J Biol Chem, 2005, pp. 4761-4771, vol. 280(6).

Wong-Riley, "Light-emitting diode treatment reverses the effect of TTX on cytochrome oxidase in neurons", Neuroreport, 2001, pp. 3033-3037, vol. 12(14).

Dörtbudak O, Haas R, Mailath-Pokorny G., Effect of low-power laser irradiation on bony implant sites, *Clin. Oral Impl. Res*, 13, 2002; 288-292.

\* cited by examiner

RED LIGHT IMPLANTS FOR TREATING OSTEOPOROSIS

CONTINUING DATA

This application claims priority and is a continuation from co-pending patent application U.S. Ser. No. 13/587,542, filed Aug. 16, 2012, entitled "Red Light Implants for Treating Osteoporosis", (Attawia), which is a continuation from U.S. Ser. No. 11/235,674, filed Sep. 26, 2005, entitled Red Light Implants for Treating Osteoporosis", (Attawia), (now U.S. Pat. No. 8,262,713, the specifications of which are incorporated by reference in their entireties.

BACKGROUND OF THE INVENTION

Osteoporosis is a disease that results in the weakening of bone and an increase in the risk of fracture. It has been reported that American females over the age of 50 have about a 50% chance of breaking a bone during their lifetime, and a 40% chance of breaking either a hip, vertebra or wrist. Post-menopausal women lose about 1-3% of their bone mass for each of the first 5-7 years after menopause. Osteoporosis is believed to contribute to about 1.5 million fractures a year in the United States, including about 700,000 spinal fractures and about 300,000 hip fractures. According to the Mayo Clinic, about 25% of the people over 50 who fracture a hip die within a year of the incident. The risk of breaking a bone for an osteoporotic individual doubles after the first fracture. The risk of breaking a second vertebra for an osteoporotic individual increases about four-fold after the first spinal fracture.

Human bone comprises hard mineralized tissue and softer collagenous tissue. The combination of these tissues provides bone with both a structural, weight-bearing capability and a shock-absorption capability. As the bone ages, however, the collagenous portion of the bone is slowly mineralized, thereby making the entire bone more brittle. To compensate for this, bone constantly undergoes a process called "remodeling" in which older, more mineralized bone is replaced by new, more collagenous bone.

Bone remodeling is undertaken by two competing processes: bone formation and bone resorption. Bone formation is largely achieved by bone-forming cells called osteoblasts, while bone resorption is largely achieved by bone-eating (bone-resorbing) cells called osteoclasts. In the normal desired situation, the rate of bone formation is essentially equal to the rate of bone resorption, so that bone mass in the body is maintained.

Osteoporosis occurs when the rate of bone resorption exceeds the rate of bone formation. The rate of bone resorption is largely dependent upon the local production of osteoclasts.

Current treatments for osteoporosis have focused upon arresting the activity of the osteoclast cells. In particular, osteoporosis therapy has focused upon administering drugs called "anti-resorptive agents" or ARA's. The most common classes of anti-resorptive drugs include estrogen, selective estrogen receptor modulators (SERMs), biphosphonates, calcitonin, osteoprotegrin (OPG), cathespin K and statins. Current products include FOSAMAX® (alendronate) in the U.S., Biphosphonate DIDRONEL® (etidronate), and ACTONEL® (risedronate).

Despite the promise provided by these anti-resorptives, there still remain serious issues. First, many anti-resorptives act in a manner that wholly eliminates osteoclast activity. Thus, the delicate balance between bone formation and bone-resorption is again upset, and older, highly mineralized tissue remains within the bone. Although this has the effect of increasing bone mineral density (BMD), the bone that remains is fragile and prone to microdamage.

Second, many of the anti-resorptives are administered systemically, through either oral or intravenous means. Accordingly, side effects associated with systemic administration are often seen. For example, the systemic administration of hormone replacement therapy ("HRT") has been associated with an elevated cancer risk. In response to this concern, some anti-resorptive drugs, such as biphosphonates, have been engineered to be selective for bone tissue. However, in many cases, the amount of such tissue selective drug that actually reaches bone is often less than 100%.

With respect to the spine, one of the manifestations of osteoporosis is the low pullout strength of pedicle screws. Simply, the lower density of the cancellous bone in the vertebral body reduces the amount of purchase available to a pedicle screw implant.

The art has described a number of different methods for enhancing the pull out strength of pedicle screws. These methods include the use of expandable screws (Cook, *Spine Journal,* 1(2001) 109-114 and Cook, *Spine Journal,* 4 (2004) 402-8), and of injectable, settable fluids around the pedicle screw (Bai, *Spine,* 26(24) 2679-83).

SUMMARY OF THE INVENTION

The present inventors have developed methods and devices for enhancing the integration of pedicle screws into vertebrae. In particular, the present inventors have developed inventions using red light irradiation of the bone-pedicle screw interface to enhance the integration of the pedicle screw into the vertebra.

The literature reports that red light irradiation enhances the pull-out strength of dental implants. For example, Khandra, *Clin. Oral Implants Res.,* 2004, Jun.: 15(3):325-332, reports that in vivo red light irradiation of dental implants increased the pullout strength of these implants by about 40%. See also, Khandra, *Swed. Dent. J. Suppl.,* 2005, (172) 1-63. Guzzardella, *Int. J. Artif. Organs,* 2001, Dec. 24(12): 898-902 reports that red light irradiation of HA nails drilled into rabbit femurs resulted in a higher degree of HA-bone integration, and concluded that low power laser treatment can be considered a good tool to enhance the bone-implant interface in orthopedic surgery.

The literature has further reported on possible reasons why red light irradiation of implants results in enhanced osteointergration. Khandra, *Clin Oral Implants Res.* 2005, Apr. 16 (2) 168-75 reports that red light irradiation of human fibroblasts cultured upon titanium implant material produces results in a significantly higher incidence of cell attachment. Lopes, *Photomed. Laser Surg.* 2005 Feb. 23 (1) 27-31 reports that red light irradiation of dental implants implanted into rabbit femurs resulted in a significant increase in calcium HA concentration. Dortbudak, *Clin. Oral Implants Res.,* 2002, Jun. 13 (3) 288-92, reports that red light irradation of wounded bone resulted in a nearly 20% increase in viable osteocyte count, while not affecting bone resorption rate.

Therefore, in accordance with the present invention, there is provided method of treating a vertebra, comprising the steps of:
 a) implanting an implant into a cancellous bone region of the vertebra, and b) irradiating the cancellous bone region with an effective amount of red light.

DETAILED DESCRIPTION OF THE INVENTION

Figure 1:
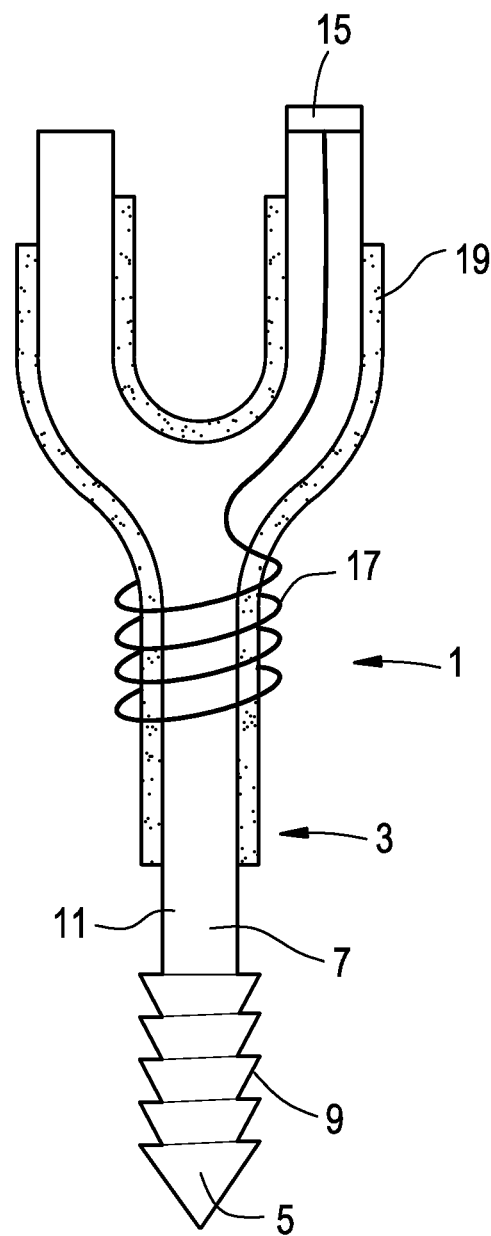
FIG. 1 discloses a glass screw embodiment of the present invention.

In some embodiments, the red light is delivered to the implant-bone interface through the pedicle screw. In these situations, it is preferred that the pedicle screw be made of a material capable of transmitting red light, such a single crystal alumina. Now referring to FIG. 1, there is provided a red light implant 1, comprising:
 a) a pedicle screw 3 made of a red light transmitting material and having:
  i) a distal tip 5,
  ii) an intermediate shaft 7 having a distal threaded portion 9 and a proximal smooth portion 11, and
  iii) a proximal end portion 13 adapted for receiving a rod or other static or dynamic fixation device (e.g., a plate or a tether),
 b) a red light LED 15 abutting the proximal portion of the screw,
 c) an Rf antenna 17 for receiving Rf energy positioned upon the proximal smooth portion of the and electrically connected to the red light LED, and
 d) a red light reflective coating 19 the proximal end portion and the proximal smooth portion of the screw.

The red light reflective coating (such as a metal) directs red light emitted by the LED distally towards the threaded portion of the screw.

In use, the screw is implanted and Rf energy is directed towards the Rf antenna portion of the implant. The Rf energy activates the LED which then emits red light, which travels throughout the screw. The red light exits the screw and irradiates the adjacent cancellous bone, thereby stimulating bone repair and osteointegration of the implant. Although the illustrated pedicle screw 3 is a monoaxial pedicle screw, the pedicle screw of the present invention can be any type of pedicle screw, including for example, a polyaxial pedicle screw.

Figure 2:
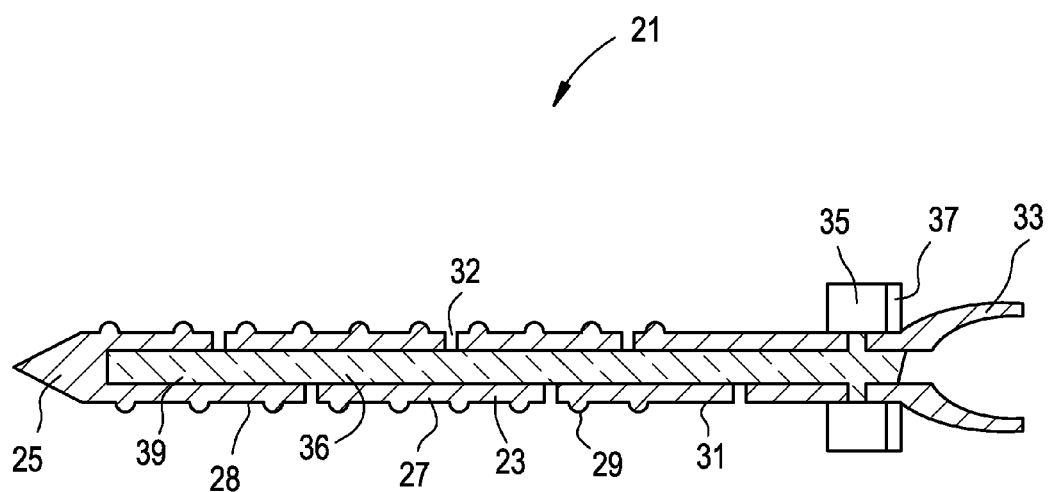
FIG. 2 discloses a cannulated screw with glass cylinder.

In other embodiments wherein the red light is delivered through the screw, the red light is delivered through a cannulated pedicle screw. Now referring to FIG. 2, there is provided a red light implant 21, comprising:
 a) a pedicle screw 23 made of a metallic material and having:
  i. a distal tip 25,
  ii. an intermediate shaft 27 having an outer surface 28 having a distal threaded portion 29, a proximal smooth portion 31 and throughholes 32,
  iii. a proximal end portion 33 adapted for receiving a rod or other static or dynamic fixation device,
  iv. a longitudinal bore 36 communicating with the throughholes,
 b) a red light LED 35 abutting the proximal portion of the screw,
 c) an Rf antenna 37 for receiving Rf energy positioned upon the proximal smooth portion of the and electrically connected to the red light LED, and
 d) a rod 39 comprising a red light transmitting material and disposed within the longitudinal bore.

Within the bore, the rod of red light transmitting material may be inserted so that red light can be shined upon the proximal end portion of the screw and delivered through the red light transmitting rod and throughholes to the cancellous regions surrounding the screw.

In some embodiments, a conventional pedicle screw is implanted and the red light is delivered via a second implant that preferably surrounds the pedicle screw In some embodiments, the second implant is a cap that rests against the proximal end of the pedicle screw.

Figure 3A:
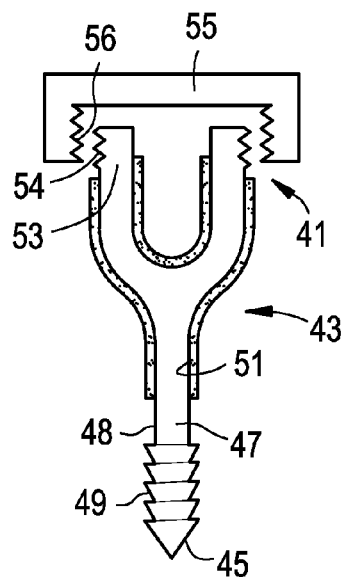
FIG. 3A-3C discloses a cap for a screw, wherein the cap transmits light through the screw.

In some embodiments, the cap transmits light through the screw. Now referring to FIG. 3a, there is provided a there is provided a red light implant 41, comprising:
 a) a pedicle screw 43 made of a red light transmitting material and having:
  i. a distal tip 45,
  ii. an intermediate shaft 47 having an outer surface 48 having a distal threaded portion 49 and a proximal smooth portion 51,
  iii. a proximal end portion 53 adapted for receiving a rod or other static or dynamic fixation device and having a threaded outer surface 54, and
 b) a cap 55 having a threaded inner surface 56 adapted to engage the threaded outer surface of the proximal end portion of the screw and made of a red light transmitting material.

In use, the cap transmits light from itself to the screw via the threaded surface interface.

Figure 3B:
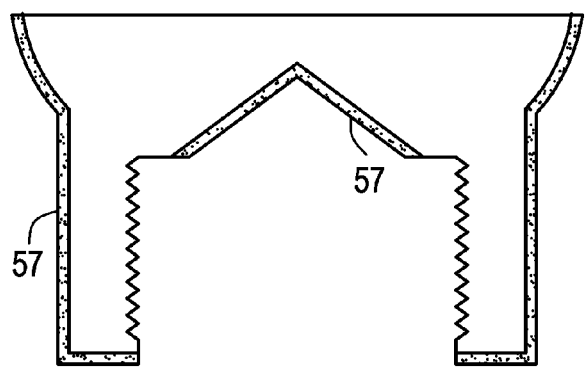

In some embodiments, and now referring to FIG. 3b, the cap is adapted to transmit red light that has been transdermally applied. Such a cap comprises a light reflective coating 57 upon the various surfaces of the cap, but has an uncoated proximal end portion that accepts the transdermally delivered light.

Figure 3C:
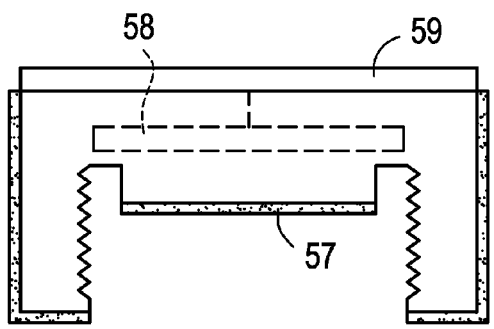

In some embodiments, and now referring to FIG. 3c, the cap contains a red light light emitting diode (LED) 58 and a power source 59 (such an antenna or battery).

Figure 4:
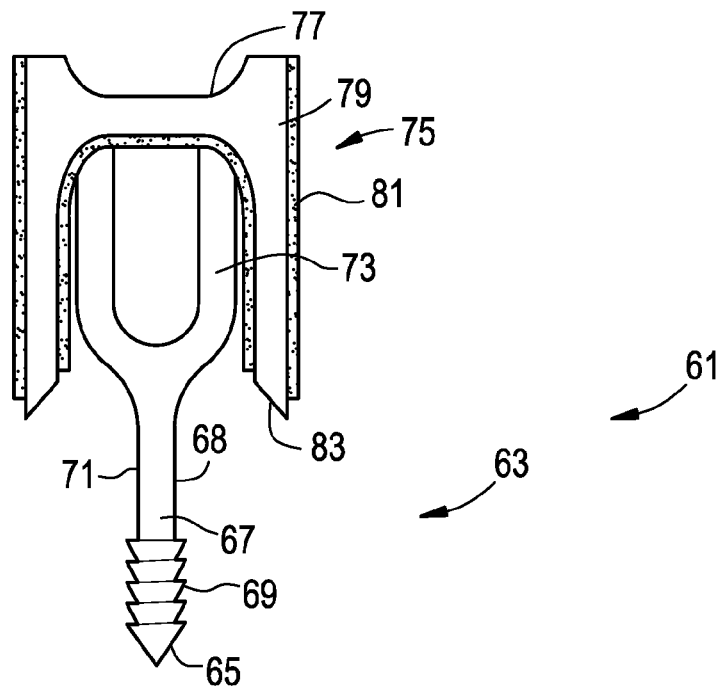
FIG. 4 discloses a cap for a screw, wherein the cap transmits light directly into bone.

Now referring to FIG. 4, there is provided a there is provided a red light implant 61, comprising:
 a) a pedicle screw 63 made of a metallic material and having:
  i. a distal tip 65,
  ii. an intermediate shaft 67 having an outer surface 68 having a distal threaded portion 69 and a proximal smooth portion 71,
  iv. a proximal end portion 73 adapted for receiving a rod, and b) a cap 75 adapted to fit around the proximal end portion of the screw and made of a red light transmitting material, the cap comprising:
  i. an uncoated distal end portion 77,
  ii. an intermediate portion 79 coated with a light reflective material 81, and
  iii. an uncoated proximal end portion 83.

Figure 5:
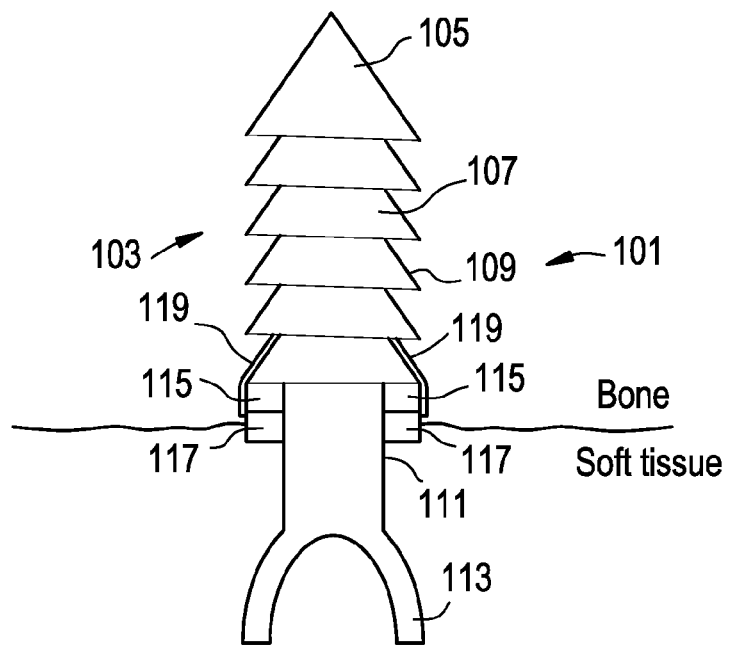
FIG. 5 discloses a collar for a screw, wherein the collar transmits light through the screw.

In some embodiments, the second implant is a collar that sits distal to the head of the screw. The collar contains a red light LED and a power source. Now referring to FIG. 5, there is provided a red light implant 101, comprising:
  a) a pedicle screw 103 made of a red light transmitting material and having:
    i) a distal tip 105,
    ii) an intermediate shaft 107 having a distal threaded portion 109 and a proximal smooth portion 111, and
    iii) a proximal end portion 113 adapted for receiving a rod,
  b) a red light LED 115 surrounding the proximal smooth portion of the shaft,
  c) an Rf antenna 117 for receiving Rf energy positioned upon the proximal smooth portion and proximal to the LED, and
  d) a red light reflective layer coating 119 covering the LED.

In some embodiments, it is preferred that the second implant has a helical shape and is implanted around the pedicle screw. The helical shape is preferred because it can be delivered in a minimally invasive manner, and can irradiate essentially the entire surface area of the pedicle screw.

Figure 6:
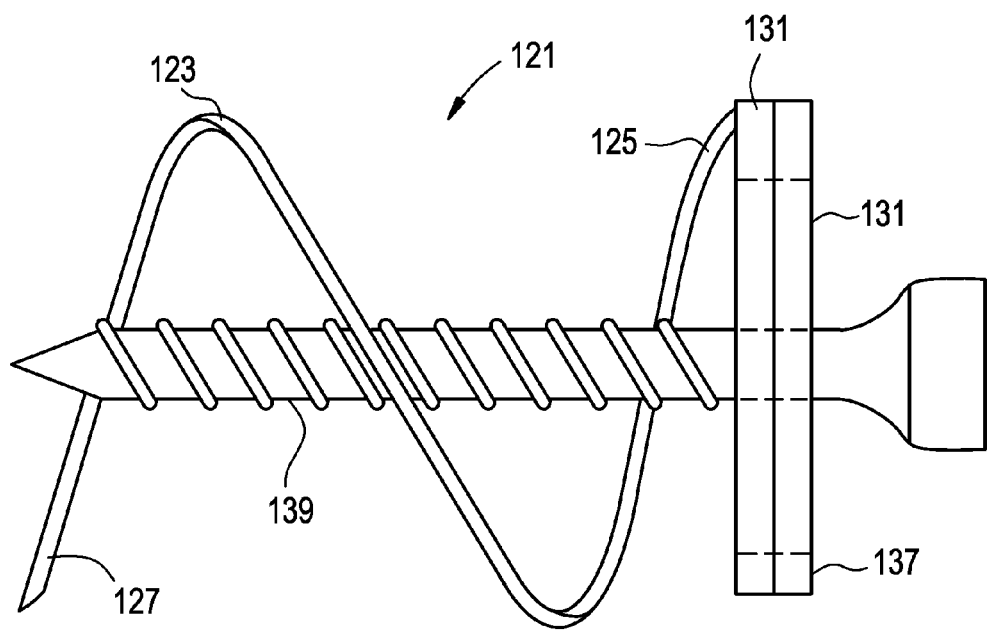
FIG. 6 discloses a helical embodiment of the present invention.

Now referring to FIG. 6, there is provided an implant 121 for delivering red light to an implant-vertebra interface, comprising:
  a) a helix 123 comprising a red light transmitting material and having a proximal end portion 125 and a distal end portion 127, and
  b) a red light source 131 connected to the proximal end portion of the helix and comprising i) a red light LED 135 and ii) a power source 137 electrically connected to the red light LED.

Still referring to FIG. 6, the helical implant is implanted in a vertebral body along with a pedicle screw 139. As shown, the helix is co-axial with the pedicle screw. The helical nature of the implant allows red light irradiation of the full diameter of the screw along its longitudinal axis.

In some embodiments, the red light implant may be a double helix in order to provide a more even illumination of the cancellous bone.

In some embodiments, the red light treatment of the present invention can be used in conjunction with the injection of a settable paste around the pedicle screw. It is believed that the red light will enhance the osteointegration of the paste to the surrounding bone.

Preferably, the settable paste comprises calcium phosphate (CaP) or hydroxyapatite (HA). As noted above, Guzzardella, *Int. J. Artif. Organs,* 2001, Dec. 24(12): 898-902 reported that red light irradiation of HA nails drilled into rabbit femurs resulted in a higher degree of HA-bone integration, and concluded that low power laser treatment can be considered a good tool to enhance the bone-implant interface in orthopedic surgery.

Therefore, in accordance with the present invention, there is provided a method of treating a vertebra, comprising the steps of:
  a) implanting an implant into the vertebra,
  b) injecting a paste around the implant, and
  c) irradiating the paste with an effective amount of red light.

Figure 7:
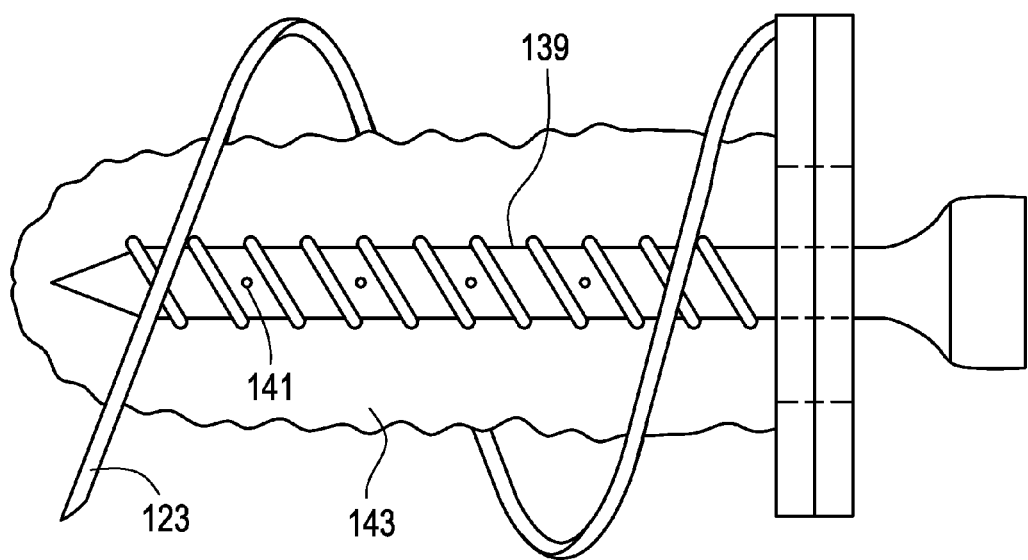
FIG. 7 discloses a helical embodiment of the present invention adapted to irradiate a pedicle screw augmented with cement.

In preferred embodiments, and now referring to FIG. 7, the pedicle screw 139 is cannulated and comprises holes 141 and the injectable, settable paste 143 is injected through the cannula of the screw and then irradiated with red light delivered from the helix 123.

Therefore, in preferred embodiments of the present invention, there is provided a method of treating a vertebra, comprising the steps of:
  a) implanting a pedicle screw having an outer surface, a central bore, and a plurality of throughholes extending between the outer surface and the central bore,
  b) injecting a settable paste into the bore so that the paste extrudes through the throughholes, and
  c) irradiating the extruded paste with an effective amount of red light.

In some embodiments, the power source can be a battery.

In other embodiments, the power source can be an Rf antenna adapted to receive Rf energy for an external Rf antenna.

In order to protect the active elements of the device from the CSF, in some embodiments, the red light LED is encased in a casing. This casing both protects the LED components from body fluids, and also prevents the LED components from eliciting a violent immune reaction In some embodiments, the casing is made of a red light transparent material. The red light transparent material may be placed adjacent the LED component so that red light may be easily transmitted therethrough. In some embodiments, the red light transparent casing is selected from the group consisting of silica, alumina and sapphire. In some embodiments, the light transmissible material is selected from the group consisting of a ceramic and a polymer. Suitable red light-transmissible ceramics include alumina, silica, CaF, titania and single crystal-sapphire. Suitable red light transmissible polymers are preferably selected from the group consisting of polypropylene and polyesters.

In some embodiments, the red light-transmissible implant comprises a red light transmissible polymer. In other embodiments, the red light-transmissible implant comprises a UVB-transmissible ceramic, such as glass. The glass content of the implant is preferably in the range of 20-40 volume percent ("v/o"). At higher glass glass contents, the implant becomes relatively inelastic. At lower implants, red light transmission is more problematic. The red light transmissible component of the implant may be in the form of beads, long fibers or chopped fibers.

In some embodiments, energy (such as Rf energy or red light) is delivered transdermally and collected near the skin layer of the patient. Such a configuration would allow light to be delivered deep within the patient, or in or near critical organs or tissues, and yet have the light source and associated components in a less sensitive region. This configuration allows easier access to the light/controller should the need arise for service or maintenance, and also allow for more efficient transdermal energy transmission. Moreover, by using a hollow tube with reflective internal surfaces, light and therapeutic fluids could be delivered to the implanted device. The light source/controller implanted near the patient's skin could also be a simple, hollow chamber made to facilitate the percutaneous access described above. The advantages and benefits of this system include:
  a) further removal from the deep site of the functional implant, thereby reducing risk of contamination of the deeper site by percutaneous access;

b) easier precutaneous access by being closer to the skin surface and having a larger surface area or target to access with the needle;
c) a larger volume could hold more therapeutic fluid to provide a longer duration of activity; and
d) a central reservoir could provide therapy to multiple implants throughout the body.

In use, the surgeon implants the implant into the spine of the patient so that the Rf receiving antenna is adjacent the posterior portion of the vertebral body.

Figure 8:
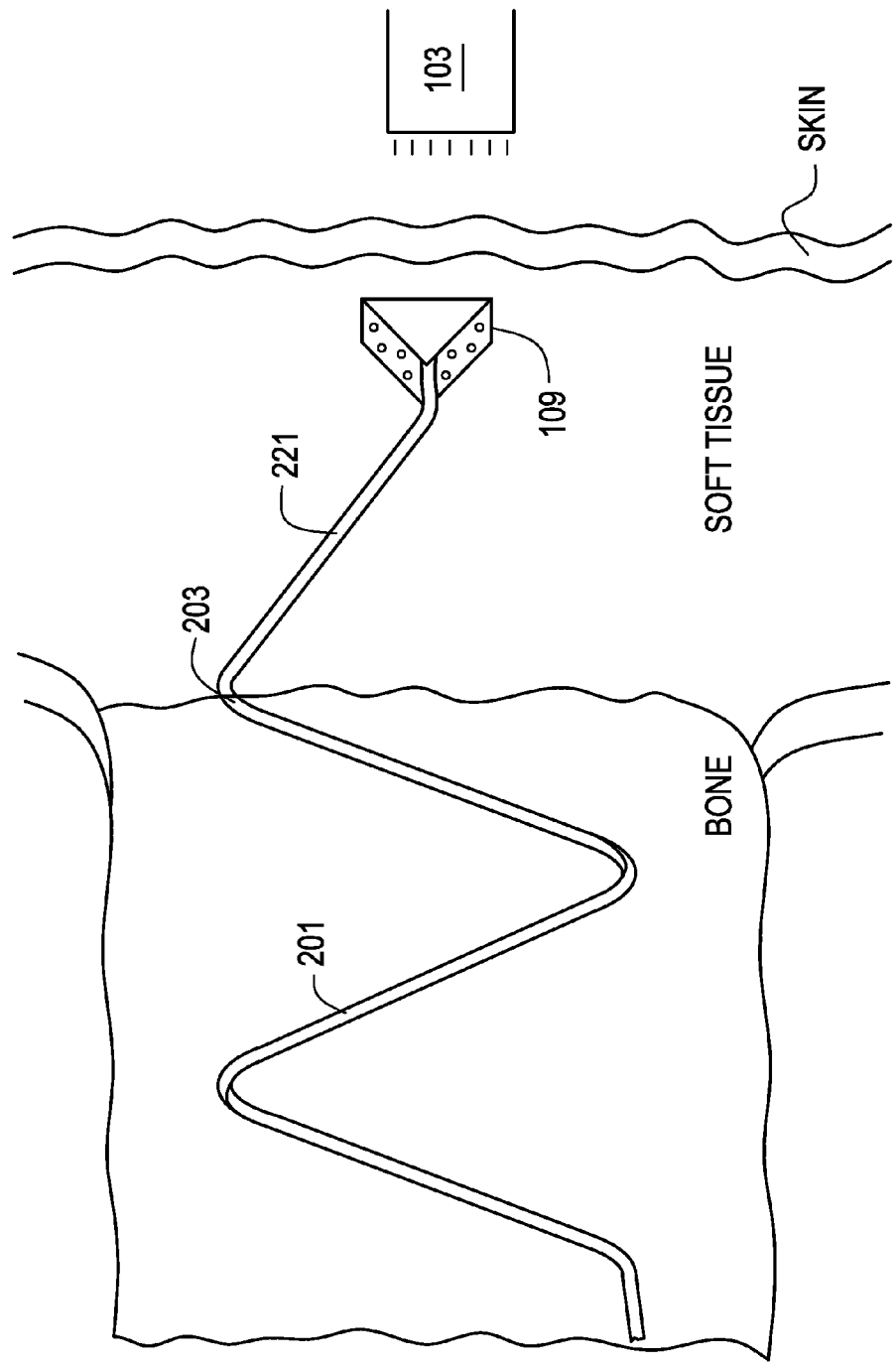
FIG. 8 discloses an exemplary implant powered by an external light source.

In some embodiments wherein the red light is delivered transdermally, it may be advantageous to provide the red light collection closer to the skin. Now referring to FIG. 8, there is provided a first exemplary implant having an external light source. The externally based-control device has a light source 101 for generating light within the device. The light generated by this source is transmitted through fiber optic cable 103 through the patient's skin to an internally-based light port 109. The light port is adapted to be in light-communication with fiber optic cable 221 disposed upon the proximal surface 203 of the helical implant 201. The helix receives the light and transmits the light to the adjacent cancellous tissue.

Figure 9:
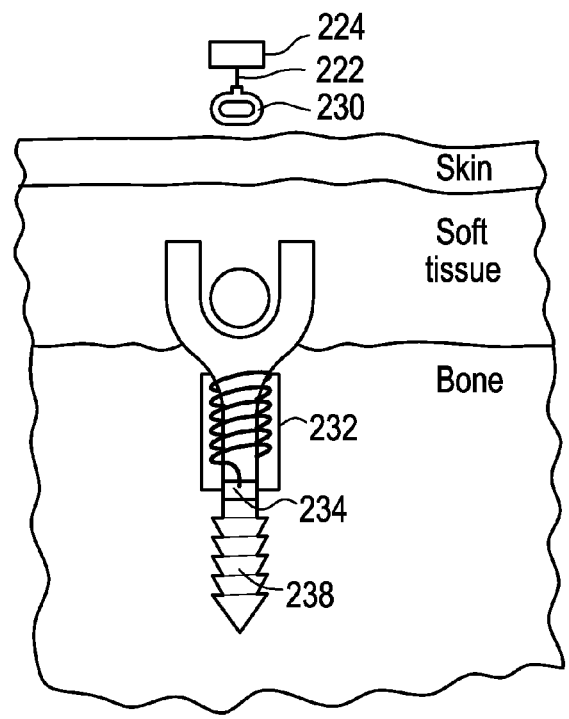
FIG. 9 discloses a red light implant of the present invention powered by an external Rf antenna.

Now referring to FIG. 9, there is provided a second exemplary UV unit having an internal light source. Externally based-control device 222 has an RF energy source 224 and an antenna 230 for transmitting signals to an internally-based antenna 232 provided on the prosthesis. These antennae 230, 232 may be electro-magnetically coupled to each other. The internal antenna 232 sends electrical power to a light emitting diode (LED) 234 disposed internally on the implant in response to the transmitted signal transmitted by the external antenna 230. The light generated by the LED travels across the red light transparent—single crystal alumina implant 238 and into the cancellous tissue.

Figure 10:
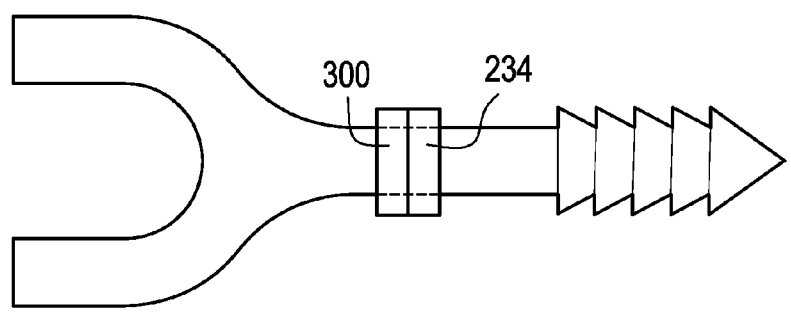
FIG. 10 discloses a red light implant of the present invention powered by an internal power source.

In some embodiments, and now referring to FIG. 10, the prosthesis having an internal light source further contains an internal power source 300, such as a battery (which could be re-chargeable), which is controlled by an internal receiver and has sufficient energy stored therein to deliver electrical power to the light source 234 in an amount sufficient to cause the desired light output.

When the implant is coupled with external energy, power can be transmitted into the internal device to re-charge the battery.

In some embodiments, the light generated by the implant is powered by wireless telemetry integrated onto or into the implant itself. In the FIG. 9 embodiment, the LED 234 may comprise a radiofrequency-to-DC converter and modulator. When radiofrequency signals are emitted by the external antenna 230 and picked up by the internal antenna 232, these signals are then converted by the receiver (not shown) into electrical current to activate the light source of the PCO unit.

In one embodiment, the implant may have an internal processor adapted to intermittently activate the LED.

In some embodiments, the telemetry portion of the device is provided by conventional, commercially-available components. For example, the externally-based power control device can be any conventional transmitter, preferably capable of transmitting at least about 40 milliwatts of energy to the internally-based antenna. Examples of such commercially available transmitters include those available from Microstrain, Inc. Burlington, Vt. Likewise, the internally-based power antenna can be any conventional antenna capable of producing at least about 40 milliwatts of energy in response to coupling with the externally-generated Rf signal. Examples of such commercially available antennae include those used in the Microstrain Strainlink™ device. Conventional transmitter-receiver telemetry is capable of transmitting up to about 500 milliwatts of energy to the internally-based antenna.

Figure 11:
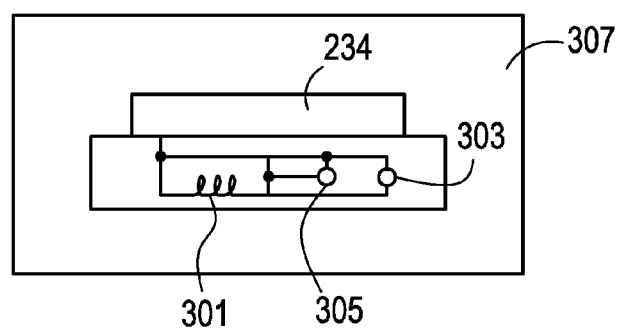
FIG. 11 discloses exemplary circuit that may accommodate an LED component of the present invention.

In some embodiments, and now referring to FIG. 11, the implant includes a light emitting diode (LED) 234 built upon a portion 307 of the implant, along with the required components to achieve trans-dermal activation and powering of the device. These components can include, but are not limited to, RF coils 301, control circuitry 303, a battery 305, and a capacitor. Such a device could be capable of intermittent or sustained activation without penetrating the skin, thereby avoiding trauma to the patient and/or risk of infection from skin-borne bacteria. As shown above, the accessory items needed to power and control the LED may be embedded within the implant. However, they could also be located on the surface(s) of the implant, or at a site adjacent to or near the implant, and in communication with the implant.

To enhance the propagation of light emitted from the end of the device, a lens could be placed at the distal end of the device to spread the light, or a diffuser such as a small sheet or plate of optical material could be used to create more surface area. Alternatively, one could create a series of lateral diffusers, such as grooves or ridges, along the distal portion of end of the device to spread light out from 360 degrees perpendicular to the axis of the device, as well as emanating directly out from the end of the fiber.

Preferably, the red light of the present invention has a wavelength of between about 600 nm and about 1000 nm. In some embodiments, the wavelength of light is between 800 and 900 nm, more preferably between 800 nm and 835 nm. In some embodiments, the wavelength of light is between 600 nm and 700 nm.

In some embodiments, the light source is situated to irradiate adjacent tissue with between about 0.02 J/cm$^2$ and 200 J/cm$^2$ energy. In some embodiments, the light source is situated to irradiate adjacent tissue with between about 0.2 J/cm$^2$ and 50 J/cm$^2$ energy, more preferably between about 1 J/cm$^2$ and 10 J/cm$^2$ energy. In some embodiments, the light source is situated to produce an energy intensity of between 0.1 watts/cm$^2$ and 10 watts/cm$^2$. In some embodiments, the light source is situated to produce about 1 milliwatt/cm$^2$.

In some embodiments, the light source emits lights consisting essentially of red light having a wavelength between 600 nm and 1000 nm. In others, the light source emits a wide spectrum of light and includes the emission of red light having a wavelength between 600 nm and 1000 nm with a strength of between about 0.02 J/cm$^2$ and 200 J/cm$^2$ energy. In one of these wide spectrum embodiments, white light is used as the light source. In some embodiments thereof, the device includes a filter that filters out at least some of the wavelengths outside of the 600-1000 nm range.

Therefore, in some embodiments of the present invention, the therapeutic dose of red light is provided on approximately a daily basis, preferably no more than 3 times a day, more preferably no more than twice a day, more preferably once a day.

In some embodiments of the present invention, the implant comprises an intervetebral motion disc and a red light source adapted to enhance the osteointegration of the endplates of the motion disc to the adjacent vertebrae.

We claim:

1. A method of treating a spine of a patient, comprising the steps of:
a) implanting an implant into a spine, and b) irradiating a bone in the spine with an effective amount of red light to induce osteointegration around the implant, wherein the light enters the bone via a transmitter located underneath the skin of the patient.

2. The method of claim 1 wherein the implant is an intervertebral implant.

3. The method of claim 1 wherein the red light is delivered in an amount effective to enhance the osteointegration of the implant.

4. The method of claim 1 wherein the red light is delivered through an LED.

5. The method of claim 1 wherein the red light has a wavelength of between about 600 nm and about 1000 nm.

6. The method of claim 1 wherein the red light irradiates a portion of the cancellous bone region with between about 0.02 J/cm$^2$ and 200 J/cm$^2$ energy.

7. The method of claim 1 wherein the implant is a screw.

\* \* \* \* \*